United States Patent [19]

Mar

[11] Patent Number: 4,512,545
[45] Date of Patent: Apr. 23, 1985

[54] EXTERNALLY ACTUATED VALVE ASSEMBLY AND METHOD

[75] Inventor: Dav Mar, Sunnyvale, Calif.

[73] Assignee: Dionex Corporation, Sunnyvale, Calif.

[21] Appl. No.: 391,571

[22] Filed: Jun. 24, 1982

[51] Int. Cl.³ ............................................. F16L 55/14
[52] U.S. Cl. ............................................ 251/4; 138/43
[58] Field of Search .......................... 251/4, 5, 6, 7, 8; 138/43, 41, 40

[56] References Cited

U.S. PATENT DOCUMENTS

| | | | |
|---|---|---|---|
| 2,422,921 | 6/1947 | Nier et al. | 251/4 |
| 4,044,991 | 8/1977 | Waller | 251/126 |
| 4,071,039 | 1/1978 | Goof | 251/7 |
| 4,176,683 | 12/1979 | Leibinsohn | 138/43 |
| 4,359,067 | 11/1982 | Cole | 251/4 |

Primary Examiner—Martin P. Schwadron
Assistant Examiner—Sheri Novack
Attorney, Agent, or Firm—Flehr, Hohbach, Test, Albritton & Herbert

[57] ABSTRACT

An externally actuated valve assembly especially suitable for use in liquid chromatography is disclosed herein. This assembly is designed to control the flow rate of a fluid through an elastomeric conduit by acting on a relatively long section of the conduit in a way which varies the cross-sectional configuration of its passageway, preferably in a uniform manner along the entire length of the passageway, in order to vary the flow rate of fluid therethrough a corresponding amount.

6 Claims, 3 Drawing Figures

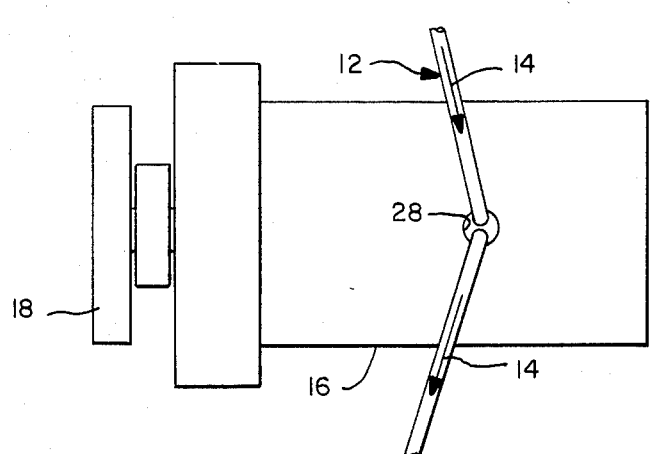
FIG.—1
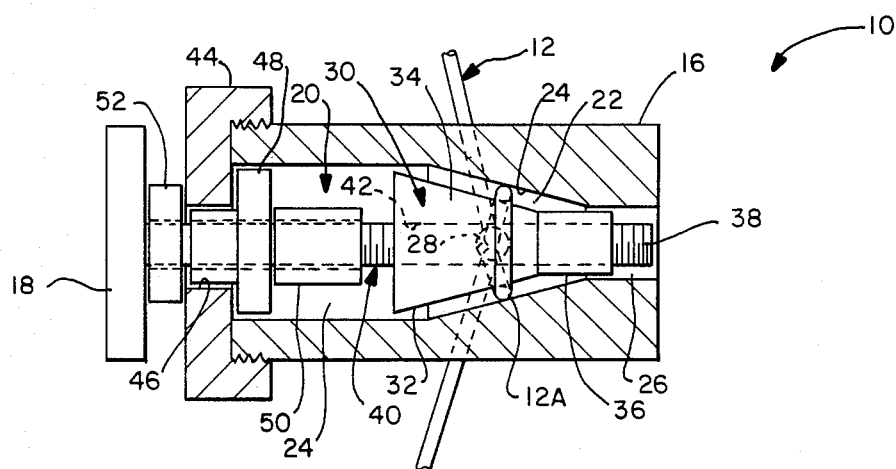
FIG.—2
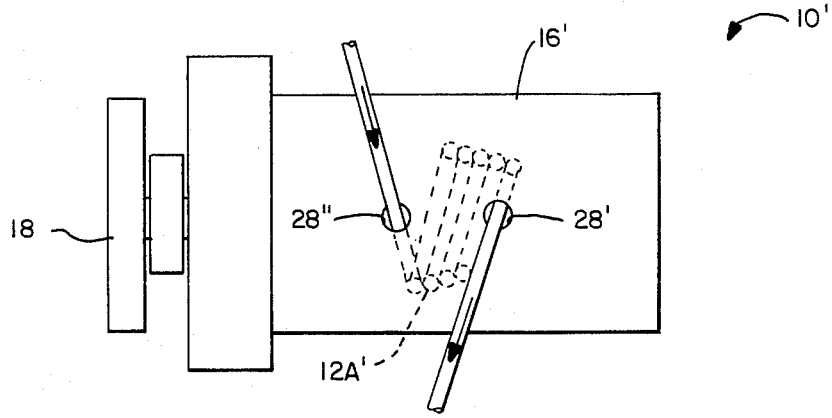
FIG—3

EXTERNALLY ACTUATED VALVE ASSEMBLY AND METHOD

The present invention relates generally to a valve of the type which functions by restricting the flow of fluid inside an elastomeric conduit by externally engaging the conduit and more particularly to one which is especially suitable for use in liquid chromatography or other technologies where the flow of fluid through relatively small volume conduits must be accurately controlled.

Presently available valve assemblies of the general type recited range from simple clamp type valves displaying limited degrees of adjustment between fully opened and fully closed positions to more complex designs which utilize multiple pinch points to create many separate orifices in order to achieve finer flow control. For applications such as liquid chromatography, the relatively uncomplicated, clamp approach does not allow for sufficiently precise flow rate adjustment, especially in the range of several milliliters per minute common to liquid chromatography technology. On the other hand, the more complicated, multiorifice approach requires too large an internal fluid volume for the degree of flow control achieved since the spaces between orifices are non-functional. In the area of liquid chromatography instrumentation, it is necessary to achieve a high degree of liquid flow control through a network of conduits while, at the same time, it is desirable to maintain the volume of these conduits at a minimum since system performance is affected thereby.

In view of the foregoing, it is one object of the present invention to provide an externally actuated valve assembly for controlling in a relatively precise fashion the flow rate of a fluid through a conduit, especially a small diameter conduit.

Another object of the present invention is to provide a valve assembly which meets the last mentioned objective in an uncomplicated, economical and yet reliable manner.

A more specific object of the present invention is to provide an externally actuated valve assembly for controlling the flow rate of a fluid through an elastomeric conduit in a way which minimizes the presence of localized stress on the conduit.

Another specific object of the present invention is to provide an externally actuated valve assembly for controlling the flow rate of a fluid through an elastomeric conduit in a way which reduces localized distrubances to its laminar flow pattern through the conduit.

Still another specific object of the present invention is to provide an externally actuated valve assembly which achieves all of the objectives recited above and yet one which is relatively compact in physical configuration.

As will be seen in more detail hereinafter, the valve assembly disclosed herein is one which acts on a specifically selected section of a conduit having an inner passageway substantially longer than it is wide. The assembly engages the external surface of this conduit section for varying the cross-sectional configuration of its passageway, preferably uniformly along the entire length of the passageway, in order to vary the flow rate of fluid therethrough a corresponding amount. In a preferred embodiment, this is accomplished by placing a conduit section between opposing surfaces of cooperating elements forming part of the assembly and varying the space between these surfaces in a uniform way.

In the particular embodiment illustrated, the valve assembly includes a means configured as a right-circular conic section having an outer conic surface serving as one of these engaging surfaces and means defining a cavity having an inner surface disposed around and corresponding in conic configuration to the outer surface and serving as a second one of the engaging surfaces. The conic section is moved along its own axis between adjustably fixed positions relative to the cavity in order to vary the spacing between opposing surfaces for squeezing the conduit section therebetween. By acting on a relatively long section of the conduit in a uniform manner, especially by means of opposing conic surfaces in the manner recited, the valve assembly of the present invention is able to control the flow rate of fluid through conduits of the type utilized in liquid chromatography instrumentation with the degree of precision necessary for such use. At the same time, of course, this valve assembly may be utilized in other technologies requiring precise fluid flow control.

A specific valve assembly which achieves the foregoing objects will be described in more detail hereinafter in conjunction with the drawing wherein:

FIG. 1 is a side elevational view of the valve assembly shown in combination with an elastomeric conduit;

FIG. 2 is an axial sectional view of the assembly shown in FIG. 1; and

FIG. 3 is a side view of the slightly modified valve assembly in combination with an elastomeric conduit.

Turning now to the drawings, wherein like components are designated by like reference numerals throughout the three figures, attention is first directed to FIG. 1 which illustrates a valve assembly 10 designed in accordance with the present invention. This assembly is shown in combination with a conduit 12 for controlling the flow rate of fluid generally indicated by arrows 14 through the conduit. The conduit may be constructed of any suitable elastomeric material including rubber, resilient plastic and the like and includes a continuous inner passageway which is preferably uniform in cross-sectional configuration along its entire length or at least along a preselected section substantially longer than it is wide. As will be described in more detail below, the valve assembly includes a main housing 16 and components therein which together act upon this preselected conduit section for varying the cross-sectional configuration of its passageway in order to vary the flow rate of fluid 14 therethrough a corresponding amount. This is accomplished by manipulating an externally located handle 18 which cooperates with the components within housing 16.

Referring specifically to FIG. 2, housing 16 is shown including axially extending, open ended cavity 20 including an intermediate cavity section 22 defined by an inner surface 24. For reasons to become apparent hereinafter, surface 24 is configured as a right-circular conic section having a preselected angle of taper extending radially inward from a larger cavity section 24 to a smaller one 26 disposed on opposite sides of section 22. These larger and smaller cavity sections are opened at opposite ends of housing 16 and the smaller cavity is square in cross-sectional configuration for reasons to be discussed while the larger one is cylindrical. A third opening 28 into the overall cavity and specifically into tapering section 22 is provided through the side wall of housing 16 for accommodating the section of conduit 12 disposed within the housing.

A pinch cone generally indicated at 30 forming part of overall valve assembly 10 is shown in FIG. 2 including a right-circular conic section 32 having an outer surface 34 corresponding in conic configuration to surface 24 of cavity section 22. Pinch cone 30 also includes a nose 36 having a square cross-sectional configuration in front of and connected to conic section 32 and serving as guide during movement of the pinch cone in the manner to be described. As seen in FIG. 2, nose 36 is slightly smaller than cavity section 26. At the same time, the maximum diameter of conic section 32 is slightly smaller than the diameter of cavity section 22.

The entire pinch cone 30 is supported within cavity 20 on a threaded shaft 38 of a screw, bolt or other such means 40 including handle 18 fixedly connected to the shaft. To this end, pinch cone 30 includes a cooperating threaded passageway 40 co-extensive with its own longitudinal axis. As seen in FIG. 2, handle 18 is located outside one end of housing 16 adjacent larger cavity section 20 and threaded shaft 38 extends into and substantially entirely through the housing cavity in coaxial relationship therewith. At the same time, square nose 36 always remains in square cavity section 26 so as to prevent the pinch cone from rotating in the cavity. In this way, by rotating handle 18 and its connected shaft 38 in one direction or the other, pinch cone 30 is caused to ride on and move axially relative to shaft 38, either in the forward direction towards cavity section 26 or rearwardly towards cavity section 24. As will be seen hereinafter, it is this particular movement that controls the flow rate of fluid through conduit 12.

Before discussing exactly how assembly 10 operates to control fluid flow through the conduit 12, attention is directed to additional components of the assembly. These include a valve cap 44 which attaches to the end of housing 16 by suitable means such as cooperating threads or the like. This valve cap includes a central opening 46 for accommodating a threaded screw retainer 48 disposed around shaft 38 and also serves as a bearing. An interally threaded limit stop/jam nut 50 which is also disposed around threaded shaft 38 between pinch cone 30 and retainer 20 locks the screw retainer to the shaft and also limits rearward axial motion of the pinch cone to prevent nose guide 36 from disengaging from cavity section 26 as the pinch cone is moved rearwardly. A spacer/retainer 52 is disposed around a section of shaft 38 outside housing 16, specifically between handle 18 and valve cap 44 and cooperates with retainer 48 for preventing axial motion of shaft 38. The spacer/retainer may or may not be interally threaded depending upon whether or not the section of shaft 38 around which it extends is threaded.

Having described valve assembly 10 from a structural standpoint, attention is now directed to the way in which this assembly controls the flow rate of fluid through conduit 12. To this end, a section of the conduit generally indicated at 12A is disposed within cavity 20 through housing opening 28. The conduit section extends around surface 34 of conic section 32 so as to make almost one complete turn at approximately a right angle with the axis of pinch cone 30. This places opposite lengthwise sides of the entire conduit section between and in engagement with confronting conic surfaces 24 and 34, as best illustrated in FIG. 2. As a result, by varying the space uniformly between these surfaces, the cross-sectional configuration of the passageway defined by conduit section 12A is varied uniformly along its length a proportionate amount, that is, between extreme conditions when the passageway is either entirely opened or completely closed. The spacing is varied between these extreme conditions by axially moving pinch cone 30 along shaft 38. In this regard, it should be noted that the amount of change in the spacing between surfaces 24 and 34 in the radial or squeezing direction is smaller but proportionate to the change in axial movement of the pinch cone along the shaft. Stated another way, the spacing between the conic surfaces varies in factional proportion to movement of the pinch cone and that is because the confronting surfaces taper. The magnitude of this fraction depends upon the amount of taper involved. In the specific embodiment illustrated, surfaces 24 and 34 define tapering angles of 30°, although this angle could vary depending upon the degree of precision required in controlling the flow rate of fluid through conduit 12. In any case, it should be quite apparent that an entire section of the conduit substantially longer than it is wide is acted upon by the valve assembly.

Referring to FIG. 3, a valve assembly 10' is illustrated. This assembly is identical to assembly 10 with one exception. Housing 16' (corresponding to housing 16) includes two openings 28' and 28'' in its side wall rather than merely one as in assembly 10. These openings are positioned to receive opposite ends of a conduit section 12A' which is acted on by the assembly in the same manner as conduit section 12A. However, conduit section 12A' is substantially longer and makes a plurality of turns around conic section 32 in a helical fashion. As a result, two openings 28' and 28'' are utilized rather than merely one opening, although a single slot could be provided in the housing. However, this is less desirable since engagement of the conduit section would be interrupted once each turn.

Whether or not the valve assembly disclosed herein acts on one turn of its associated conduit or a plurality of turns, it should be apparent that the conduit section acted upon is relatively long (compared to its diameter). This minimizes the occurrence of localized stresses and it reduces localized disturbances to laminar flow which is especially important in the field of liquid chromatography. These advantages are attained whether or not the conduit section acted upon is helically wrapped and whether or not the particular conic configuration is utilized. By helically wrapping the conduit section acted upon, the entire valve assembly utilized may be made more compact and by utilizing the conic configuration, the assembly can control the flow rate through the conduit in a more precise fashion. In this latter regard, one of the means for moving pinch cone axially within cavity 20 may be manually actuated handle 18. This could be achieved by means of weights, springs, toggles, pneumatic or hydraulic pistons or any other suitable means.

What is claimed is:

1. A valve assembly for controlling the flow rate of a fluid through an elastomeric conduit including a section thereof having an inner pasageway, said assembly comprising: first means configured as a right-circular conic section having an outer conic surface adapted to support said section of conduit such that the latter makes at least one turn around said surface at approximately a right angle with one axis of the conic section, second means defining a cavity having an inner surface disposed around and corresponding in conic configuration to said outer surface with a spacing therebetween for accommodating said conduit section; and means for moving said conic section along its conic axis between adjustably fixed positions relative to said cavity in order to change the spacing between said inner and outer surfaces for squeezing said conduit section and changing the cross-sectional configuration of its passageway a proportionate amount, whereby to control the flow rate of fluid therethrough.

2. An assembly according to claim 1 wherein said cavity defining means includes opening means for accommodating said conduit as the latter enter and exits the cavity with said conduit section therein.

3. An assembly according to claim 2 wherein said opening means consists of a single opening for receiving both the entering and exiting ends of said conduit section and wherein the latter makes only one turn around the outer surface of said conic section.

4. An assembly according to claim 2 wherein said conduit section makes a plurality of turns around the outer surface of said conic section whereby opposite ends of said section are axially spaced from each other along said outer surface, and wherein said opening means includes a pair of spaced apart holes for respectively receiving the opposite ends of said conduit section.

5. A method of controlling the flow rate of a fluid through an elastomeric conduit comprising the steps of: selecting a section of said conduit having an inner passageway which is substantially longer than it is wide, providing first and second members having opposing first and second surfaces, one of said surfaces being movable along a predetermined path relative to the other of said surfaces, moving said one surfaces, relative to the other along said path for engaging opposite sides of the external surface of said conduit section in a way which varies uniformly the cross-sectional configuration of said passageway along its entire length an amount less then but proportionate to the movement of said one surface along said path in order to vary the flow rate of fluid through the passageway a corresponding amount, and supporting said conduit section about a plurality of helical turns of a curved path as opposite sides of its external surface are engaged.

6. A valve assembly for controlling the flow rate of a fluid through an inner passageway of an elastomeric conduit, said assembly comprising: means defining first and second uniformly spaced apart, confronting curved surfaces for engaging a continuous lengthwise section of said conduit on opposite sides thereof in a way which compresses said sides into a segment of said inner passageway defined by said conduit section; and means for varying the spacing between said curved surfaces uniformly and in a controlled manner in order to vary uniformly the cross-sectional configuration of said passageway segment a proportionate amount and thereby control the flow rate of fluid through said passageway; the conduit section within the spacing between said curved surfaces extending lengthwise in a curved fashion corresponding to the curves of said surfaces; said means defining said curved surfaces including means configured as a conic section having an outer conic surface serving as said first surface and means defining a cavity having an inner surface serving as said second surface disposed around and corresponding in conic configuration to said inner surface; and said space varying means including means for moving said conic section axially into and out of said cavity.

* * * * *